(12) United States Patent
Kim

(10) Patent No.: US 10,468,561 B2
(45) Date of Patent: Nov. 5, 2019

(54) LED MODULE FOR INCREASING EFFECTIVE WAVELENGTHS OUTPUT

(71) Applicant: Cellreturn Co., Ltd., Bucheon-si (KR)

(72) Inventor: Ilsoo Kim, Bucheon-si (KR)

(73) Assignee: Cellreturn CO., LTD., Bucheon (KR)

( * ) Notice: Subject to any disclaimer, the term of this patent is extended or adjusted under 35 U.S.C. 154(b) by 0 days.

(21) Appl. No.: 16/102,769

(22) Filed: Aug. 14, 2018

(65) Prior Publication Data

US 2019/0058090 A1    Feb. 21, 2019

(30) Foreign Application Priority Data

Aug. 17, 2017   (KR) .................. 10-2017-0103896

(51) Int. Cl.

| | |
|---|---|
| *H01L 33/50* | (2010.01) |
| *F21V 19/00* | (2006.01) |
| *A61N 5/06* | (2006.01) |
| *H01L 33/62* | (2010.01) |
| *H01L 33/44* | (2010.01) |
| *H01L 33/58* | (2010.01) |
| *H01L 33/64* | (2010.01) |

(52) U.S. Cl.
CPC .......... *H01L 33/502* (2013.01); *A61N 5/0616* (2013.01); *F21V 19/001* (2013.01); *H01L 33/44* (2013.01); *A61N 2005/0626* (2013.01); *A61N 2005/0651* (2013.01); *A61N 2005/0659* (2013.01); *H01L 33/58* (2013.01); *H01L 33/62* (2013.01); *H01L 33/642* (2013.01)

(58) Field of Classification Search
CPC ..... H01L 33/502; H01L 33/504; H01L 33/44; A61N 5/0616; A61N 2005/0651
See application file for complete search history.

(56) References Cited

U.S. PATENT DOCUMENTS

| | | | |
|---|---|---|---|
| 6,396,082 B1 * | 5/2002 | Fukasawa | ............. H01L 33/486 257/100 |
| 8,138,673 B1 * | 3/2012 | Wedding | ................. H01J 47/02 313/567 |

(Continued)

FOREIGN PATENT DOCUMENTS

| | | |
|---|---|---|
| JP | 4330742 | 9/2009 |
| KR | 100390968 | 7/2003 |
| KR | 101412617 | 6/2014 |

OTHER PUBLICATIONS

Written Opinion (machine translation), Korean Pat. App. No. 10-2017-0103896, KIPO, dated Feb. 21, 2018, all pages. (Year: 2018).*

*Primary Examiner* — Victoria K. Hall
(74) *Attorney, Agent, or Firm* — Patent Office of Dr. Chung Park

(57) ABSTRACT

An LED module for increasing effective wavelengths output includes a light emission unit configured to be supplied with electric energy to generate light; and a frame unit where an installation space for installing the light emission unit is formed, and that absorbs electromagnetic waves being generated in the light emission unit. During operation, harmful electromagnetic waves other than the effective waves beneficial to human body may be absorbed. Accordingly, even when the human body is exposed to the LED module for a long period of time, the side effects caused by the electromagnetic waves can be minimized.

6 Claims, 2 Drawing Sheets

(56) References Cited

U.S. PATENT DOCUMENTS

| | | | |
|---|---|---|---|
| 8,471,470 B1* | 6/2013 | Wedding | H01J 47/02 |
| | | | 313/567 |
| 10,242,954 B2* | 3/2019 | Kawabata | H01L 23/552 |
| 2008/0179503 A1* | 7/2008 | Camargo | H01L 31/0203 |
| | | | 250/216 |
| 2015/0171281 A1* | 6/2015 | Nakabayashi | H01L 33/486 |
| | | | 257/98 |
| 2018/0132390 A1* | 5/2018 | Jeong | H05K 1/095 |
| 2018/0162098 A1* | 6/2018 | Joo | H01L 23/3733 |

* cited by examiner

[Fig. 1]
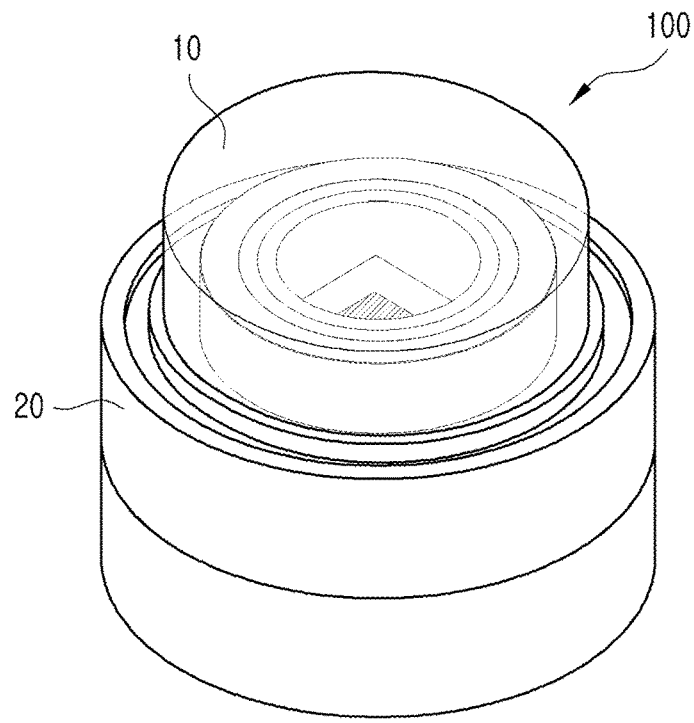
[Fig. 2]
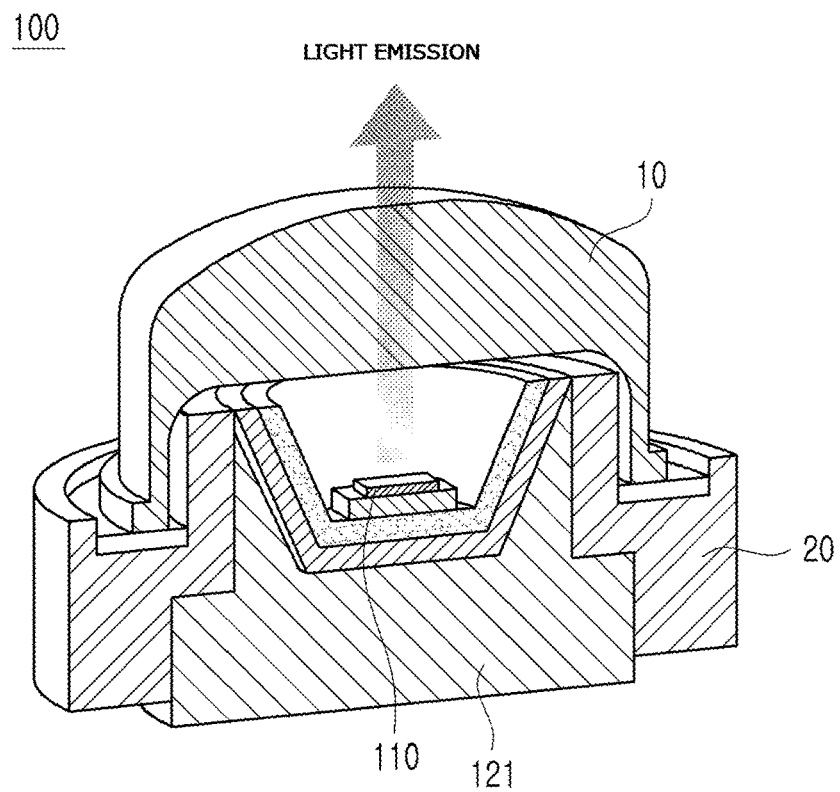

[Fig. 3]
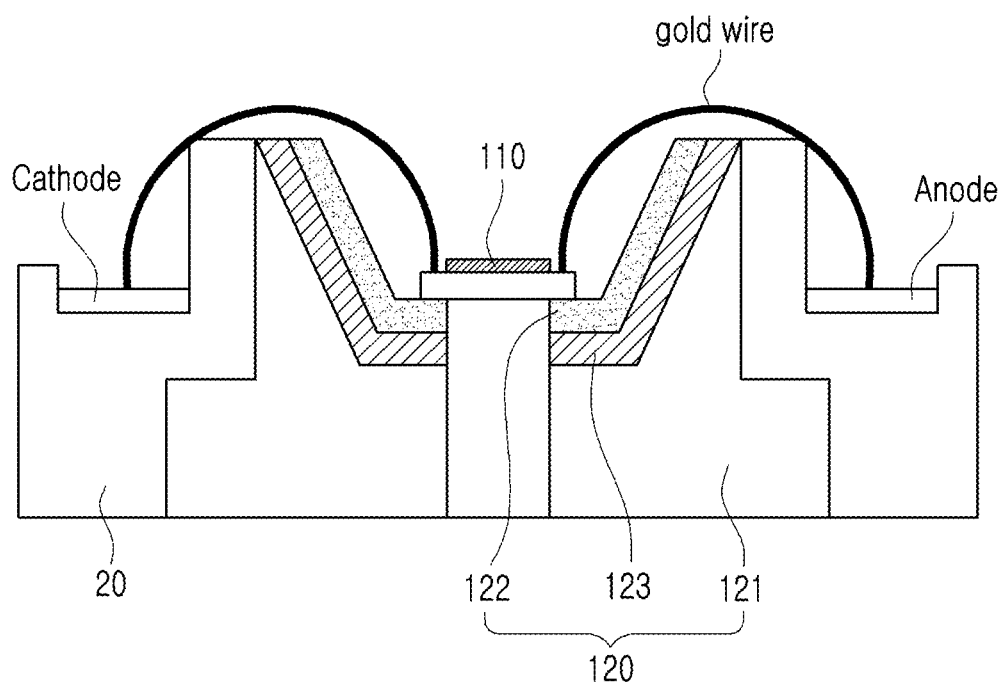
[Fig. 4]
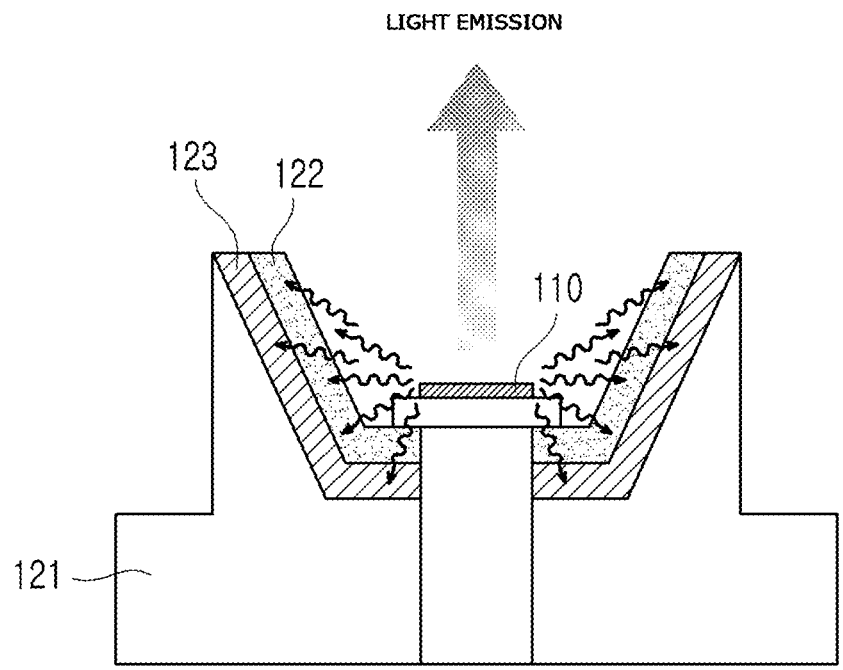

LED MODULE FOR INCREASING EFFECTIVE WAVELENGTHS OUTPUT

TECHNICAL FIELD

The present invention relates to an LED module for increasing effective wavelengths output, and more particularly, to an LED module for increasing effective wavelengths output, capable of effectively absorbing harmful electromagnetic waves being generated when a light emission unit emits light, thereby outputting effective wavelengths only.

BACKGROUND OF THE INVENTION

Infrared light has a long wavelength, and thus the scattering effect caused by particles is small. Therefore, there is a great effect of penetrating into human body, and it becomes possible to heat a skin surface layer and an inner layer evenly at the same time, thus leading to great skin care and medical treatment effect.

Recently, as it has been widely known that infrared light is effective in regenerating skin and treating various diseases, various devices using LED modules that generate infrared light are being studied and developed.

An LED module generates infrared light that is beneficial to human body, and at the same time, it discharges electromagnetic waves that are harmful to the human body. Therefore, when using a skin care device or treatment device that uses an LED module, and thus human body is exposed to electromagnetic waves for a long period of time, side effects caused by the electromagnetic waves, that is, various diseases such as sleep disorder, indigestion, headache, sterility and the like can occur.

SUMMARY OF THE DISCLOSURE

Therefore, a purpose of the present disclosure is to solve the aforementioned problems of prior art, that is, to provide an LED module for increasing effective wavelengths output, capable of effectively absorbing harmful electromagnetic waves being generated when a light emission unit emits light, thereby outputting effective wavelengths only.

According to the present disclosure, the above purpose is achieved by the LED module for increasing effective wavelengths output, that may include the light emission unit that is configured to be supplied with electric energy to generate light; and a frame unit where an installation space for installing the light emission unit is formed and that is configured to absorb electromagnetic waves being generated in the light emission unit.

Further, the frame unit may include a substrate layer, a first absorption layer where the installation space is formed and that is made of a conductive material, and a second absorption layer that is installed between the first absorption layer and the substrate layer and that is made of a magnetic material so as to absorb the electromagnetic waves.

Further, the first absorption layer may absorb the electromagnetic waves by generating induced current on a surface by the electromagnetic waves and generating thermal energy as the induced current is applied to an internal resistance.

Further, the first absorption layer may be provided to include polypyrole or polyaniline.

Further, the second absorption layer may be subject to magnetic relaxation by the electromagnetic waves to absorb the electromagnetic waves.

Further, the second absorption layer may be made to include ferrite.

According to the present disclosure, during the light emission in the light emission unit, harmful electromagnetic waves, other than the effective wavelengths that are beneficial to human body, may be absorbed. Accordingly, even when the human body is exposed to the LED module for a long period of time, the side effects caused by the electromagnetic waves can be minimized.

BRIEF DESCRIPTION OF THE DRAWINGS

FIG. 1 illustrates a perspective view of an LED module for increasing effective wavelengths output according to an embodiment of the present disclosure;

FIG. 2 illustrates a cross-sectional view of the LED module for increasing effective wavelengths output according to an embodiment of the present disclosure;

FIG. 3 illustrates a side cross-sectional view of the LED module for increasing effective wavelengths output according to an embodiment of the present disclosure; and FIG. 4 illustrates a process in which a frame unit of the LED module for increasing effective wavelengths output absorbs the electromagnetic waves being generated in the light emission unit according to an embodiment of the present disclosure.

DETAILED DESCRIPTION OF THE PREFERRED EMBODIMENTS

Hereinbelow, some embodiments of the present disclosure will be explained in detail with reference to exemplary drawings. It should be noted that in adding reference numerals to the configurative elements in each drawing, identical configurative elements were made to have identical reference numerals as much as possible, even if they are indicated in other drawings.

Further, in explaining the embodiments of the present disclosure, if it is determined that a related well-known configuration or function interrupts understanding the embodiments of the present disclosure, detailed explanation of the well-known configuration or function shall be omitted.

Further, in explaining the configurative elements of the embodiments of the present disclosure, terms such as a first, a second, A, B, (a), (b) and the like may be used. Such terms are merely for distinguishing between those configurative elements and other configurative elements, and do not limit the essence, sequence or order of corresponding configurative elements.

Hereinbelow, an LED module for increasing effective wavelengths output according to an embodiment of the present disclosure will be explained in detail with reference to the drawings attached.

FIG. 1 illustrates a perspective view of the LED module for increasing effective wavelengths output according to an embodiment of the present disclosure; FIG. 2 illustrates a cross-sectional view of the LED module for increasing effective wavelengths output according to an embodiment of the present disclosure; FIG. 3 illustrates a side cross-sectional view of the LED module for increasing effective wavelengths output according to an embodiment of the present disclosure; and FIG. 4 illustrates a process in which a frame unit of the LED module for increasing effective wavelengths output absorbs the electromagnetic waves being generated in the light emission unit according to an embodiment of the present disclosure.

As illustrated in FIGS. 1 to 4, the LED module for increasing effective wavelengths output according to an embodiment of the present disclosure 100 includes a light emission unit 110, a frame unit 120 and a control unit.

The light emission unit 110 is configured to be supplied with electric energy to generate light, and is installed in an installation space that is formed by the frame unit 120 that will be explained hereinafter.

The aforementioned light emission unit 110 may include three light sources, that is, three LEDs. Each light source may be provided to form a different wavelength range. That is, for example, a first light source may be provided as an LED that outputs wavelengths between 460 nm and 470 nm, a second light source may be provided to output wavelengths between 620 nm and 680 nm, and a third light source may be provided to output wavelengths between 760 nm and 900 nm.

The infrared light wavelengths between 460 nm and 470 nm are known to have an effect of vitalizing skin surface cells and increasing the blood flow rate to vitalize skin tissues, thereby greatly increasing skin regeneration, the infrared light wavelengths between 620 nm and 680 nm are known to have an effect of keeping the skin surface cells clean to prevent any skin troubles such as acne, folliculitis and the like, and the infrared light wavelengths between 760 nm and 900 nm are known to have an effect of further improving the above effects when used together with the light having the two wavelengths ranges mentioned above.

Therefore, according to the light emission unit 110 that includes the first light source, the second light source and the third light source, there is an effect of treating and preventing various skin diseases effectively.

According to the infrared light being emitted from the light emission unit 110 as aforementioned, skin diseases can be prevented as aforementioned, but when infrared light is being generated in the light emission unit 110, electromagnetic waves that are harmful to human body can be generated as well.

When the electromagnetic waves are emitted to the human body for a long period of time, various diseases such as sleep disorder, indigestion, headache, sterility and the like can occur. Therefore, the electromagnetic waves that are generated during operation of the light emission unit 110 need to be removed.

The frame unit 120 is where an installation space for installing the aforementioned light emission unit 110 is formed, and that absorbs the electromagnetic waves being generated in the light emission unit 110. The frame unit 120 is accommodated in a cover 10 and a main body 20.

The aforementioned frame unit 120 includes a substrate layer 121, a first absorption layer 122 and a second absorption layer 123.

The substrate layer 121 provides a space for forming the first absorption layer 122 and the second absorption layer 123. The substrate layer 121 may be made of a synthetic resin material, and may include cerium, tourmaline and germanium.

Cerium (Ce) has an atomic number of 58, and is a rare-earth element that belongs to the lanthanum group. Cerium (Ce) has a characteristic of absorbing ultraviolet light of or below 400 nm, and is thus used in ultraviolet light sterilizing devices or sunglass lens.

Tourmaline is a mineral that belongs to the hexagonal system group, having crystalline structures such as quartz. It is a borosilicate consisting of iron, magnesium, alkali metal and aluminum. Such a tourmaline has a characteristic where anions are generated by irregular movement of internal atoms.

Germanium (Ge) has an atomic number of 32, and is a carbon group element that belongs to the fourteenth group in the periodic table and cycle four. It has a rectifying characteristic, and is thus widely used in rectifiers, transistors, semiconductors and the like.

As aforementioned, cerium has a characteristic of absorbing ultraviolet light, tourmaline has an effect of generating anions and thus offsetting electromagnetic waves, and germanium has an effect of absorbing electromagnetic waves due to its rectifying characteristic. Therefore, in the case of mixing cerium, tourmaline and germanium in an appropriate ratio to form the substrate layer 121, there is an effect where by the first absorption layer 122 and the second absorption layer 123 that will be explained hereinafter, the electromagnetic waves remaining after the absorption and the electromagnetic waves in low frequency range can be absorbed and removed in the substrate layer 121 (third absorption).

The first absorption layer 122 is made of a conductive material so as to primarily absorb the electromagnetic waves being generated in the light emission unit 110. The installation space for installing the light emission unit 110 is formed in the first absorption layer 122, and the first absorption layer is installed on an upper surface of the second absorption layer 123 that will be explained hereinafter.

In the case where the electromagnetic waves enter into a conductive material, induced current is generated on the surface, and herein, the generated induced current is applied to the resistance inside the conductive material, and accordingly, thermal energy is generated in the resistance. According to the aforementioned process, the electromagnetic waves that entered into the conductive material are exchanged in the form of thermal energy, and are consequently removed.

It is desirable that such a conductive material is made of polymer that includes polypyrole or polyaniline. That is because, in the case of such a conductive material, conductivity is adjusted according to the doping extent (that is, it is possible to adjust the electromagnetic waves absorption wavelength range), and in the case of the conductive material based on polypyrole or polyaniline, doping is relatively easy.

Meanwhile, the reason why the first absorption layer 122 made of conductive material is formed on an uppermost surface of the frame unit 120 is because, that way, thermal energy can be easily discharged outside.

According to the first absorption layer 122 as that aforementioned, the electromagnetic waves being generated in the light emission unit 110 may be primarily absorbed, and may thus be removed in the form of thermal energy.

The second absorption layer 123 is made of a magnetic material so as to secondarily absorb the electromagnetic waves being generated in the light emission unit 110. The second absorption layer 123 is installed between the aforementioned substrate layer 121 and the first absorption layer 122.

In the case where the electromagnetic waves enter into magnetic material, the magnetic material becomes subject to magnetic relaxation in a certain frequency range (between MHz and GHz) and absorbs the electromagnetic waves.

It is desirable that such a magnetic material is provided to include ferrite. That is because not only does the magnetic material based on ferrite have a wide electromagnetic wave absorption range but it is also easily processible to be produced in a layer form.

According to the aforementioned second absorption layer 123, the electromagnetic waves being generated in the light emission unit 110 may be secondarily removed. Herein, the electromagnetic waves being removed have a high frequency range.

According to the frame unit 120 that includes the substrate layer 121, the first absorption layer 122 and the second absorption layer 123 as aforementioned, first of all, the electromagnetic waves being generated in the light emission unit 110 are primarily absorbed in the first absorption layer 122 as a whole, and then the electromagnetic waves of a high frequency range are secondarily absorbed again in the second absorption layer 123, and then the electromagnetic waves of a low frequency range are tertiarily absorbed again in the substrate layer 121. Therefore, according to the frame unit 120, harmful electromagnetic waves of various wavelengths other than the effective wavelengths being generated in the light emission unit 110, that is, those of the infrared light range can be effectively absorbed.

Although not illustrated in the drawings, the control unit is configured to control the aforementioned light emission unit 110, and may be electrically connected to and installed in the main body 20.

Such a control unit adjusts the infrared light wavelengths being emitted to a user's body by selectively lighting one or more of the aforementioned first light source, the second light source and the third light source according to the user's operation.

Further, the control unit may receive information on the infrared light wavelengths currently being generated from the light emission unit 110, and transmit the information to an external terminal (possessed by the user). According to such a control unit, there is an effect where the user can easily grasp information on the infrared light wavelengths currently being generated in the light emission unit 110.

Further, the control unit may be provided to be operated remotely by the aforementioned terminal. According to such a control unit, there is an effect where the user can easily adjust the infrared light wavelengths remotely using the terminal that he/she uses, instead of operating the control unit directly.

According to the LED module for increasing effective wavelengths output according to an embodiment of the present disclosure 100 that includes the light emission unit 110, the frame unit 120 and the control unit as aforementioned, when the light emission unit 110 emits light, harmful electromagnetic waves other than the effective wavelengths (between 460 nm and 900 nm) can be effectively absorbed. Accordingly, even if the human body is exposed to the LED module for a long period of time, the side effects caused by the electromagnetic waves can be minimized.

In the aforementioned, just because it is explained that all the configurative elements composing the embodiments of the present disclosure are combined as one or operate in combination does not mean that the present disclosure is limited to such embodiments. That is, as long as they are within the range of purpose of the present disclosure, one or more of all those configurative elements may be selectively combined and operate.

Further, terms such as "include", "comprises" or "has/have" and the like disclosed above have been used to indicate that their subsequent configurative elements may internally exist, and thus it should be construed that other configurative elements can be further included, not that other configurative elements are excluded. All terms including technical or scientific terms have the same meanings as those generally understood by a person with ordinary knowledge in the art that the present disclosure belongs to, unless defined otherwise. Generally used terms such as those defined in dictionaries must be construed as corresponding to contextual meanings of the related art, and must not be construed ideally or overly formally, unless explicitly defined in the present disclosure.

Further, the explanation above is merely an exemplary explanation of the technical concept of the present disclosure, and thus a person skilled in the related art could make various modifications and alterations within the range that does not go beyond the essential characteristics of the present disclosure.

Therefore, the embodiments in the present disclosure are not intended to limit the technical concept of the present disclosure, but to explain the present disclosure, and the range of the technical concept of the present disclosure is not limited by such embodiments either. The protection range of the present disclosure must be construed by the claims below, and should be construed such that all the technical concepts within the equivalent range are included in the scope of right of the present disclosure.

What is claimed is:

1. An LED module for increasing effective wavelengths output, comprising:
    a light emission unit configured to be supplied with electric energy to generate light; and
    a frame unit configured to provide an installation space for installing the light emission unit,
    wherein the frame unit includes a substrate layer, a first absorption layer where the installation space is formed and a second absorption layer installed between the first absorption layer and the substrate layer,
    wherein the first absorption layer is made of a conductive material and the second absorption layer is made of a magnetic material.
2. The LED module according to claim 1, wherein the first absorption layer comprises polypyrole or polyaniline.
3. The LED module according to claim 1, wherein the second absorption layer comprises ferrite.
4. The LED module according to claim 1, wherein the substrate layer comprises at least one of cerium, tourmaline and germanium.
5. The LED module according to claim 1, wherein the light emission unit includes a plurality of light sources.
6. The LED module according to claim 5, wherein each of the plurality of light sources has a different wavelength range.

* * * * *